(12) United States Patent
Magagnoli et al.

(10) Patent No.: US 11,833,051 B2
(45) Date of Patent: Dec. 5, 2023

(54) ACETABULAR SPACER DEVICE COMPRISING A PHARMACEUTICAL SUBSTANCE

(71) Applicant: Cossington Limited, Kingston upon Thames (GB)

(72) Inventors: Augusto Magagnoli, Cervia (IT); Robert Michael Meneghini, McCordsville, IN (US); Bryan Donald Springer, Charlotte, NC (US); Scott Matthew Sporer, Wheaton, IL (US); Stephen Joseph Incavo, Houston, TX (US)

(*) Notice: Subject to any disclaimer, the term of this patent is extended or adjusted under 35 U.S.C. 154(b) by 14 days.

(21) Appl. No.: 15/733,524

(22) PCT Filed: Mar. 7, 2018

(86) PCT No.: PCT/IB2018/051480
§ 371 (c)(1),
(2) Date: Aug. 19, 2020

(87) PCT Pub. No.: WO2019/171138
PCT Pub. Date: Sep. 12, 2019

(65) Prior Publication Data
US 2020/0383789 A1 Dec. 10, 2020

(51) Int. Cl.
*A61F 2/30* (2006.01)
*A61F 2/34* (2006.01)

(52) U.S. Cl.
CPC ............. *A61F 2/30724* (2013.01); *A61F 2002/30672* (2013.01); *A61F 2002/30677* (2013.01); *A61F 2002/30879* (2013.01); *A61F 2002/3425* (2013.01); *A61F 2310/00221* (2013.01); *A61F 2310/00353* (2013.01)

(58) Field of Classification Search
CPC ........ A61F 2/30724; A61F 2002/30672; A61F 2002/30677; A61F 2002/30879; A61F 2002/3425; A61F 2310/00221; A61F 2310/00353; A61F 2002/30881; A61F 2310/00005; A61F 2310/00179; A61F 2/34; A61F 2/30767; A61F 2/30771; A61L 27/14; A61L 27/54; A61L 2430/24
See application file for complete search history.

(56) References Cited

U.S. PATENT DOCUMENTS 4,883,490 A    11/1989  Oh
4,936,863 A *   6/1990  Hofmann .................. A61F 2/32
                                           623/23.26
(Continued)

FOREIGN PATENT DOCUMENTS

WO       2014072076      5/2014

*Primary Examiner* — Brian A Dukert
*Assistant Examiner* — Melissa A Hoban
(74) *Attorney, Agent, or Firm* — Themis Law

(57) ABSTRACT

An acetabular spacer device, of a type that is temporary and disposable, adapted to be implanted in use in a bone cavity placed at a joint of the human body, such as a hip or shoulder joint, has a cup-like shape, substantially hemispherical, and includes a first convex surface, adapted to be positioned at the bone cavity, a second concave surface, which defines a cavity, further includes at least one pharmaceutical or medical substance, such as at least one antibiotic, adapted to treat during use an ongoing infection in the bone cavity.

14 Claims, 4 Drawing Sheets

(56) References Cited

U.S. PATENT DOCUMENTS

| | | | |
|---|---|---|---|
| 5,658,338 A | 8/1997 | Tullos | |
| 5,931,870 A * | 8/1999 | Cuckler | A61F 2/34 623/22.21 |
| 6,626,949 B1 * | 9/2003 | Townley | A61L 27/303 623/23.39 |
| 7,108,720 B2 * | 9/2006 | Hanes | A61F 2/32 623/22.21 |
| 7,758,653 B2 * | 7/2010 | Steinberg | A61F 2/30771 623/23.5 |
| 7,955,395 B2 * | 6/2011 | Shea | A61F 2/4637 623/22.28 |
| 8,679,187 B2 * | 3/2014 | Allen | A61F 2/34 623/22.24 |
| 9,138,320 B2 * | 9/2015 | Forsell | A61F 2/34 |
| 2003/0171818 A1 * | 9/2003 | Lewallen | A61F 2/30767 623/22.22 |
| 2005/0080490 A1 * | 4/2005 | Bertram, III | A61F 2/34 623/22.28 |
| 2005/0085915 A1 * | 4/2005 | Steinberg | A61F 2/3609 623/17.16 |
| 2005/0261777 A1 * | 11/2005 | Jones | A61F 2/30771 623/22.32 |
| 2008/0009953 A1 * | 1/2008 | Ling | A61F 2/4684 623/22.21 |
| 2009/0093887 A1 * | 4/2009 | Walter | A61F 2/32 623/22.11 |
| 2009/0130167 A1 * | 5/2009 | Shelton | A61F 2/30728 424/423 |
| 2010/0042213 A1 * | 2/2010 | Nebosky | A61B 17/60 623/16.11 |
| 2010/0185298 A1 | 7/2010 | Stone | |
| 2012/0109137 A1 * | 5/2012 | Iannotti | A61B 17/1728 606/87 |
| 2012/0179270 A1 * | 7/2012 | Nevins | A61F 2/34 623/22.35 |
| 2014/0303743 A1 * | 10/2014 | Choudhury | A61F 2/32 623/22.24 |
| 2016/0089156 A1 * | 3/2016 | Fortin | A61B 17/1666 606/81 |
| 2016/0235955 A1 * | 8/2016 | Magagnoli | A61F 2/389 |
| 2020/0237517 A1 * | 7/2020 | Roy | A61F 2/34 |

* cited by examiner

ACETABULAR SPACER DEVICE COMPRISING A PHARMACEUTICAL SUBSTANCE

TECHNICAL FIELD OF THE INVENTION

The present invention relates to an acetabular spacer device, adapted to be implanted in a corresponding cavity of the human body.

In particular, the acetabular spacer device is, of a temporary and disposable type, and is used for the treatment of a bone site subject to infection, in view of the implant of a prosthesis or of a new prosthesis.

PRIOR ART

The term "acetabolum" relates in general to a recess or cavity of the human body in which the condyle of a nearby moving organ is inserted.

For example, the acetabulum present in the pelvis at the hip joint is also called "cup" and is formed by the fusion of ileum, ischium and pubis; it constitutes a joint cavity and is able to articulate with the head of the femur (coxofemoral joint).

The glenoid cavity of the scapula is also present in the human body: it is a shallow, articular surface that is articulated with the head of the humerus (glenohumeral joint).

Following traumas or pathologies of the joints of the human body, it is possible to intervene by implanting a permanent prosthesis.

It can also happen that infections occur on the joint site and in this case, both if a prosthesis is already present on the site and if it is the patient's bone tissue, it is necessary to eradicate the bacterial outbreak by treatment with pharmaceutical or medical substances, such as for example antibiotics (possibly removing the present prosthesis).

The spacer device according to the present invention aims at this objective, with particular reference to the bone tissues surrounding the articular cavity, both in the case of infection occurring in the patient's bone tissue and following the implantation of a permanent prosthesis.

OBJECTS OF THE INVENTION

The task of the present invention is to improve the prior art.

Within the scope of this technical task, it is an object of the present invention to provide an acetabular spacer device for the treatment of an infection occurring at a joint cavity of the human body.

A further object of the present invention is to provide an acetabular spacer device adapted to restore the shape of the cavity on which it is implanted and thus improve the joint with the head of a femur or of a humerus or with the head of respective prosthetic components or of hip or shoulder spacer devices.

Another object of the present invention is to provide an acetabular spacer device having shape or dimensions corresponding to the anatomical shape or dimensions of the patient.

According to one aspect of the present invention, an acetabular spacer device according to claim 1 is provided.

The dependent claims refer to preferred and advantageous embodiments of the invention.

BRIEF DESCRIPTION OF THE DRAWINGS

Further features and advantages of the present invention will appear more clearly from the detailed description of a preferred but non-exclusive embodiment of an acetabular spacer device, given by way of a non-limiting example in the accompanying drawings, in which.

EMBODIMENTS OF THE INVENTION

Figure 1:
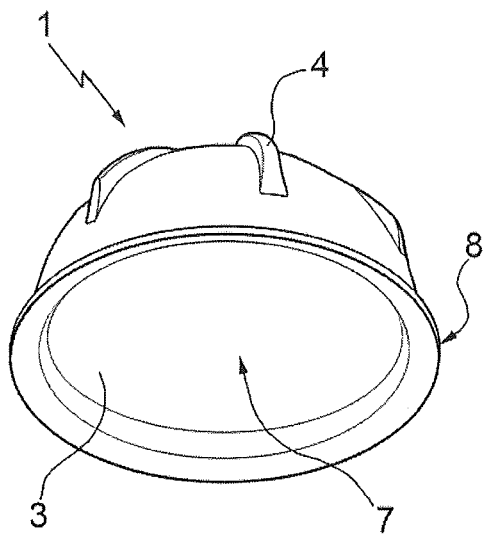
FIG. 1 is a perspective bottom view of the acetabular spacer device according to a first version of the invention.
Figure 2:
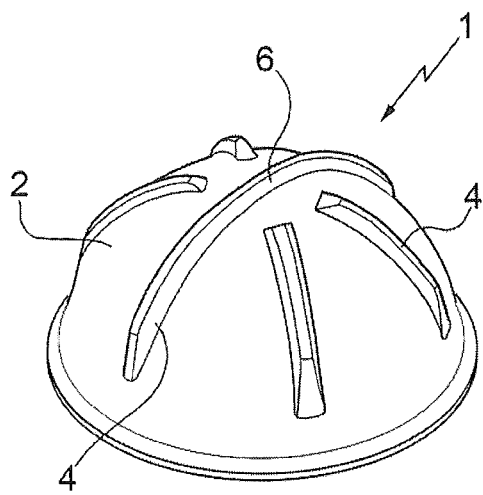
FIG. 2 is a perspective top view of the acetabular spacer device in FIG. 1.
Figure 3:
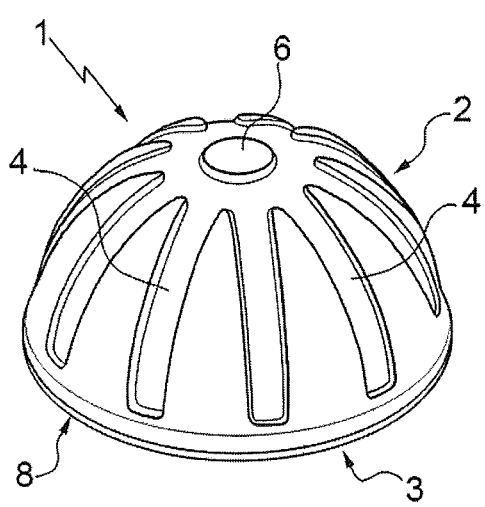
FIG. 3 is a perspective top view of the acetabular spacer device according to a second version of the invention.
Figure 4:
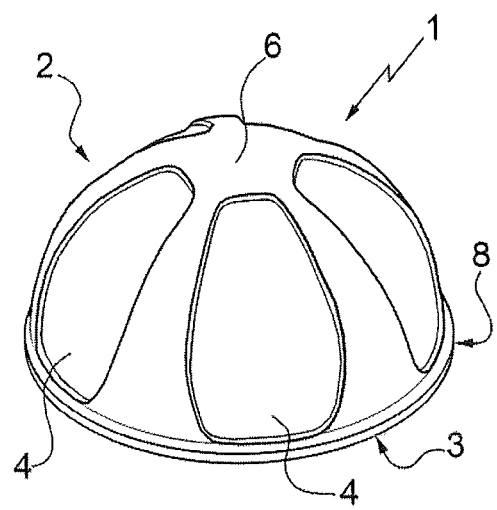
FIG. 4 is a perspective top view of the acetabular spacer device according to a third version of the invention.

With reference to the figures, 1 globally indicates an acetabular spacer device according to the present invention.

The acetabular spacer device 1 is a disposable and temporary spacer device, suitable for treating an infection occurred at the implantation site.

The acetabular spacer device 1 is adapted to be implanted in use in a bone cavity located at a joint of the human body, such as a hip or shoulder joint, thus for example at the cotyloid cavity of the joint of the hip or at the glenoid cavity of the shoulder joint.

In the illustrated images, in particular, an acetabular spacer device 1 is shown for the treatment of a hip joint and/or for the replacement of a hip prosthesis, but the present invention can also be referred to devices for treating other types of bone sites and/or for the replacement of other types of prostheses, for example, seats or prostheses of the humerus, seats or prostheses of ankle, elbow, etc.

The acetabular spacer device 1 according to the invention is suitable for being implanted, if necessary, in place of a permanent prosthesis previously inserted at the respective joint or seat, which has undergone infection.

Furthermore, the acetabular spacer device 1 is adapted to articulate with the head of the femur, with the head of the humerus, with a corresponding prosthetic component or with a corresponding spacer device, for example with the stem component of a respective joint.

The acetabular spacer device 1 according to the present invention includes at least one pharmaceutical or medical substance, such as at least one antibiotic, capable of combating an infection in place at the implantation site.

The acetabular spacer device 1 has a cup shape, that is to say, a substantially hemispherical shape.

In particular, the acetabular spacer device 1 has a first surface 2, that is convex, suitable for being positioned at the acetabular cavity of the patient's bone, and a second surface 3, that is concave.

The second surface 3 is adapted to articulate with the head of a femur, of a humerus or with corresponding components of a permanent prosthesis or a spacer device, for example with the femoral or humeral stem of a spacer device or of a permanent prosthesis.

At the first surface 2, the acetabular spacer device 1 comprises a plurality of elongated projections or recesses 4, extending outwardly or inwardly (with respect to the first surface 2) of the acetabular spacer device 1 itself.

In particular, the first surface 2 has such a shape and dimensions as to adapt to the patient's acetabulum or bone cavity, since it has a shape substantially complementary to that of the bone cavity.

The second surface 3, on the other hand, has such a shape and dimensions that it allows the housing and the articulation of the head of the respective component, in consideration of the joint in which the acetabular spacer device 1 is in use inserted.

The second surface 3, moreover, is completely smooth, precisely to facilitate the articulation and the rotation/sliding of the head of the respective component.

Entering more in detail, the acetabular spacer device 1 has—as said—a cup-shaped configuration, in which the first and second surfaces 2, 3 are substantially semi-spherical.

In a version of the invention, the first surface 2 and the second surface 3 are coaxial, and in particular have the same central symmetry axis X, which corresponds to that of the acetabular spacer device 1.

The acetabular spacer device 1, according to a version of the invention, comprises a base 5, perpendicular to the central symmetry axis X of the device itself.

The base 5 is formed by a base ring 5a which connects the first surface 2 and the second surface 3, in particular the terminal circular perimeter of the first end 2 and the terminal circular perimeter of the second end 3.

The base 5 also delimits an opening 5b which delimits the gap or inlet opening towards the second surface 3 and/or the gap or inlet opening of the cavity 7 defined by the second surface 3 which is convex.

The cavity 7 has a substantially hemispherical conformation.

The opening 5b, as well as the base 5, have a substantially circular or annular shape.

Therefore, the first surface 2 and the second surface 3 have a shape corresponding to that of a spherical base cap 5.

The area of connection between the base ring 5a and the second surface 3 can be tapered or rounded, so as to avoid the presence of sharp edges in the articulation area with a further component present in the articular cavity in question.

The acetabular spacer device 1 further comprises an apex 6, placed at the top of the acetabular spacer device 1 and/or of the first surface 2. The apex 6 is opposite to the base 5.

The central symmetry axis X of the device 1 passes at the apex 6.

At the terminal circular perimeter of the first surface 2 there is an annular tab 8. The annular tab 8 extends externally with respect to the acetabular spacer device 1.

The tab 8 projects outwardly from the surface 2 by a portion Z.

In particular, the annular tab 8 and/or the section Z extends substantially perpendicular to the first surface 2 and/or coplanar with respect to the base 5 of the acetabular spacer device 1.

The annular tab 8 acts as an abutment or support for the patient's articular seat and/or acetabular bone. In this way, the stability of the positioning or implantation of the acetabular spacer device 1 is increased.

The acetabular spacer device 1 may have a hemisphere shape, and in this case the base 5 corresponds to the equatorial plane of the sphere which corresponds to the acetabular spacer device 1 or it may continue beyond it, and the base 5 will in this case be smaller than that of the equatorial plane of the sphere that corresponds to the acetabular spacer device 1. Alternatively, the acetabular spacer device 1 may have a smaller shape than that of a hemisphere, and the base 5 also in this case will have a smaller area than that of the equatorial plane of the sphere which corresponds to the acetabular spacer device 1.

Equatorial plane means a plane perpendicular to the central symmetry axis X of the articular component 2 and passing through a diameter thereof.

As already mentioned, the acetabular spacer device 1, or rather the first surface 2 thereof, comprises a plurality of elongated projections or recesses 4. These elongated projections or recesses extend towards the outside or towards the inside of the acetabular spacer device 1, with respect to the surface 2 itself.

The elongated projections or recesses 4 substantially depart from the apex 6 or from the area surrounding the apex 6, up to the terminal peripheral area of the first surface 2 and/or the annular tab 8.

In one version, for example shown in FIGS. 1, 2 and 5-9, the first surface 2 has elongated projections 4, which extend towards the outside of the acetabular spacer device 1, therefore—in use—towards the bone of the patient.

In the second and third versions of the acetabular spacer device 1, for example shown respectively in FIGS. 3, 10-12 and 4, 13-15, the first surface 2 has elongated recesses 4, which extend towards the inside of the device acetabular spacer 1, therefore—in use—away from the patient's bone.

Figure 5:
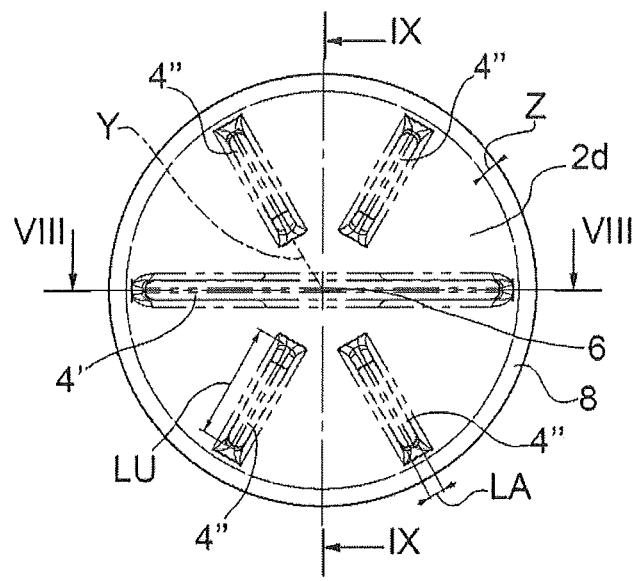
FIG. 5 is a top view of the acetabular spacer device in FIGS. 1 and 2.
Figure 6:
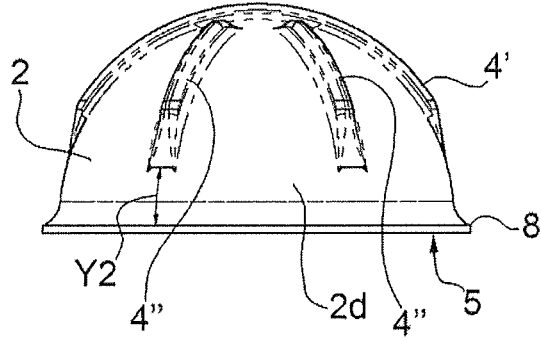
FIG. 6 is a front view of the acetabular spacer device in FIGS. 1, 2 and 5.

In the version for example shown in FIG. 5, it is seen that a first elongated projection 4' extends along a maximum circumference section of the acetabular spacer device 1. The first projection 4', therefore, has the shape of an axis of circumference that passes through the apex 6. The other or second elongated projections 4" develop in a radial pattern from the apex 6.

Figure 7:
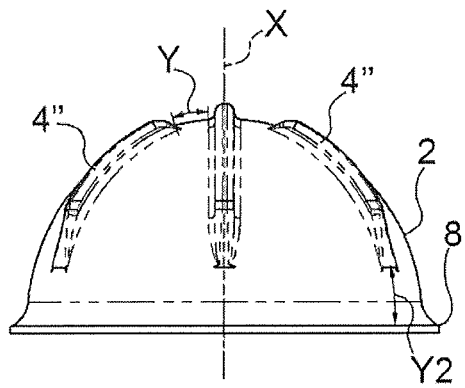
FIG. 7 is a side view of the acetabular spacer device in FIGS. 1, 2 and 5.

In particular, in a version, these second elongated projections 4" branch off from an area surrounding the apex 6, that is to say, they are spaced from it by a portion Y, as can be seen in FIG. 5. As can be seen in FIG. 7, the section Y is a curved section which follows the pattern of the first surface 2.

The first and second projections 4', 4" have an elongated shape, that is to say, they have a length LU greater than their width LA. They can have a substantially rectangular shape, possibly with rounded corners.

Moreover, the ends of the first and second projections 4', 4" are rounded or tapered towards the surface 2, and/or connected thereto in a degrading manner, in order to avoid the presence of sharp edges at the surface of the acetabular spacer device 1 which will come into contact with the bone tissue.

Moreover, the first and second projections 4', 4" extend upwards with respect to the first surface 2 by a section or height H.

In at least one embodiment example, H is substantially corresponding to the measure LA while the measure LU is much greater than the measure of LA or H.

For example, for the second projections 4" LU is at least 5 times LA and the first projection 4' has a measure equal to twice or thrice the second projection 4".

In one version of the invention (not shown), there may be two first projections 4', placed perpendicularly with respect to one another or in an incident manner with respect to each other at the apex 6.

As can be seen in the accompanying figures, the projections 4', 4", at least in one embodiment, are equally spaced from one another.

The end of the first and second protrusions 4', 4" (opposite to that present at the apex 6) terminates at the terminal perimeter area of the first surface 2 and/or of the annular tab 8 and, in particular, at a distance Y2 with respect to the same.

Figure 8:
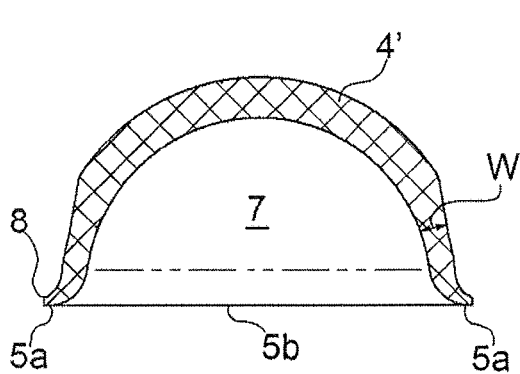
FIG. 8 is a sectional view of the acetabular spacer device along the section plane VIII-VIII in FIG. 5.
Figure 9:
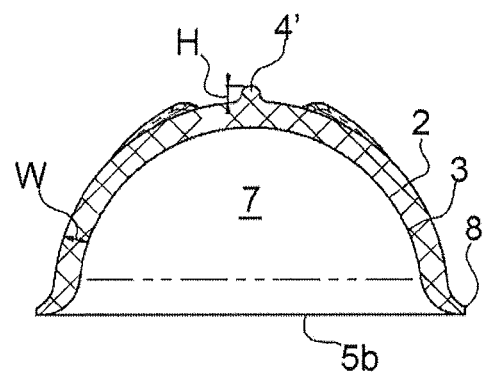
FIG. 9 is a sectional view of the acetabular spacer device along the section plane IX-IX in FIG. 5.

As can be seen, for example, in FIGS. 8 and 9, the thickness W of the acetabular spacer device 1 is given by the thickness of the wall constituting the device itself, and therefore by the distance between its first surface 2 and its second surface 3.

This shape of the elongated projections 4', 4" delimits corresponding angular sectors 2d of surface 2, having a substantially triangular shape, having a vertex at the area of the apex 6 and having as a base a section of the terminal perimeter of the first surface 2 itself. Each angular sector 2d is delimited laterally by two elongated projections 4" or by a first projection 4' and by a second projection 4".

In one version of the invention, this thickness W is substantially constant along the entire extension of the acetabular spacer device 1.

As can be seen in FIG. 8, the projections 4', 4" are made in one piece with the acetabular spacer device 1 and therefore the latter, corresponding to the areas in which the projections 4', 4" are positioned, has a thickness equal to W+H.

The first projection 4' substantially cuts the first surface 2 of the acetabular spacer device 1 into two same halves.

In the embodiment illustrated by way of example only, in the device 1 there is a projection 4' and two projections 4" for each half (of the acetabular spacer device 1) identified precisely by the projection 4', for a total of four second projections 4".

Alternatively, from 2 to 10 second projections 4" may be present, possibly arranged symmetrically with respect to the first projection 4'.

In the embodiment in FIGS. 3 and 10-12, as said, the first surface 2 has elongated recesses 4, which are retracted towards the inside of the acetabular spacer device 1.

Figure 10:
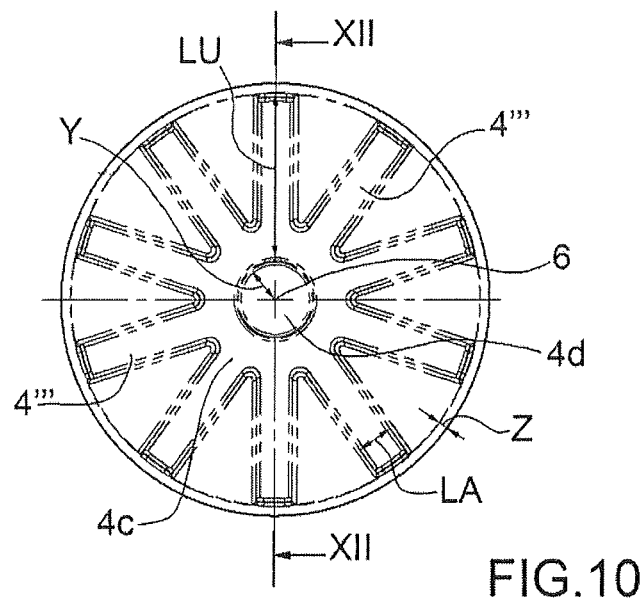
FIG. 10 is a top view of the acetabular spacer device in FIG. 3.
Figure 11:
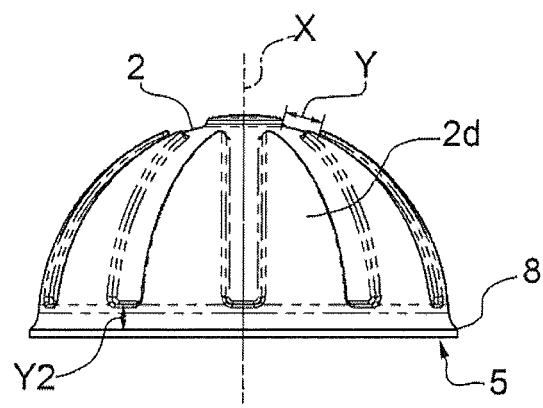
FIG. 11 is a front view of the acetabular spacer device in FIGS. 3 and 10.

Considering the version in FIG. 10, the recesses 4 comprise elongated recesses 4''' having a substantially rectangular shape, possibly with rounded corners.

Figure 12:
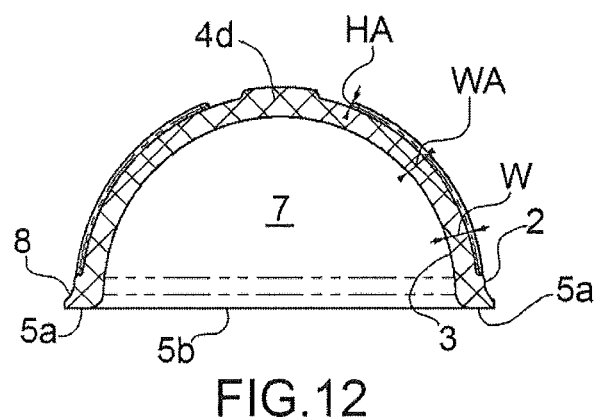
FIG. 12 is a sectional view of the acetabular spacer device along the section plane XII-XII in FIG. 10.
Figure 13:
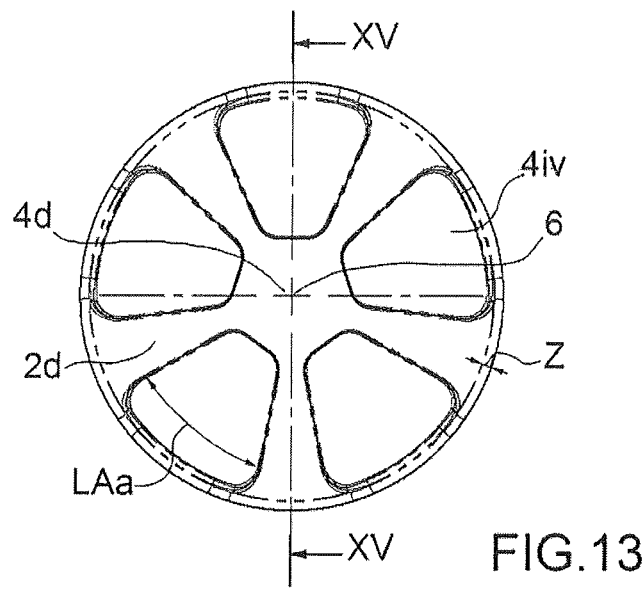
FIG. 13 is a top view of the acetabular spacer device in FIG. 4.
Figure 14:
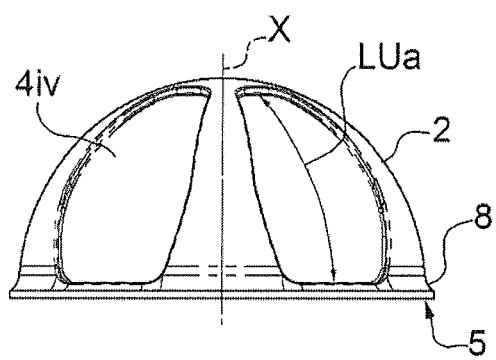
FIG. 14 is a front view of the acetabular spacer device in FIGS. 4 and 13.
Figure 15:
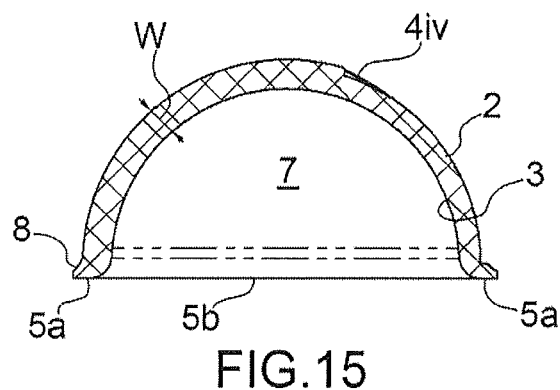
FIG. 15 is a sectional view of the acetabular spacer device along the section plane XV-XV in FIG. 13.

As visible, for example, in FIG. 12, therefore, the thickness W of the acetabular spacer device 1 is equal to WA at the areas in which the recesses 4 are positioned, with WA smaller than W. In particular, the recesses extend towards the inside with respect to the first surface 2 by a section HA. Thus, the recesses 4 of the version in FIG. 3 have a depth HA. Therefore, WA is equal to the measure of W reduced by HA.

The end closest to the vertex 6 of each elongated recess 4''' branches off at a distance Y from the vertex 6.

The recesses 4''' are arranged radially around the apex 6 and, in at least one version of the invention, are equidistant from one another.

Therefore, as can be seen in the accompanying figures, the recesses 4''' have the shape of a recessed groove having a curved shape, substantially corresponding to that of the first surface 2 but recessed with respect to the latter.

The positioning of the recesses 4''' is such that their ends closest to the vertex 6 are close to each other, delimiting a sort of recessing groove 4c around the area of the apex 6, having a substantially circular and annular shape.

At the apex 6, in this way, a zone 4d of the first surface 2, having a substantially circular shape, is delimited.

This shape of the elongated recesses 4''' delimits corresponding angular sectors 2d of surface 2, having a substantially triangular shape, having a vertex at the groove 4c and having as a base a section of the terminal perimeter of the first surface 2 itself. Each angular sector 2d is delimited laterally by two elongated recesses 4'''.

In the illustrated version, only by way of example, in the acetabular spacer device 1 there are ten elongated recesses 4'. Alternatively, there may be present from 6 to 16 elongated recesses 4'''.

The recesses 4''', where not expressly indicated, substantially have the same features of the projections 4, 4', 4" of the previously described version, but instead of being projecting towards the bone, they are recessed with respect to the first surface 2.

Finally, in an analogous manner, in the embodiment shown in FIGS. 4 and 13-15, elongated recesses 4iv are shown, which have the same features as the previously described version but vary in shape.

In fact, the recesses 4iv have a substantially polygonal shape, for example trapezoidal or ovoid, in which the width LAa grows away from the apex 6 towards the circular terminal perimeter of the first surface 2 and/or towards the circular tab 8.

In the other versions, the width LA of the projections or recesses 4', 4", 4''' was substantially constant along their whole extension.

Furthermore, the elongated recesses 4iv have a length LUa substantially equal to 1-2 times the maximum width LAa (that considered at the circular terminal perimeter of the first surface 2) thereof.

As described above, at the apex 6 there is a zone 4d, of first surface 2, having a circular or polygonal shape, whose number of sides—in this last case—is equal to the number of elongated recesses 4iv.

In fact, in the area of the apex 6, the ends of the recesses 4iv comprise a side (for example the smaller base of a trapezium) of the polygon which constitutes the recess 4iv itself.

Moreover, the elongated recesses 4iv define angular sectors 2d, of first surface 2, having a substantially triangular or trapezoidal shape, with a vertex or smaller base at the area 4d and greater base at a portion of the circular terminal perimeter of the first surface 2.

In order to perform its infection healing and treatment function, the acetabular spacer device 1 comprises at least one pharmaceutical or medical substance, such as for example an antibiotic.

The material constituting the acetabular spacer device 1, therefore, is a porous material and/or provided with canaliculi, capable of absorbing and/or eluting such at least one pharmaceutical or medical substance, and then releasing it in contact with the bone tissue in which an infection has developed.

Since that according to the present invention is a temporary acetabular spacer device 1, it must not remain permanently inside the human body. Therefore, it must be removed once it has performed its healing function against possible infections that arise at the implantation site. Therefore, any pores and/or canaliculi present therein have dimensions such as to prevent growth of the bone tissue within them. Therefore, in at least one version of the invention, any pores and/or canaliculi are smaller than 100 microns or micrometers.

One of the functions of the pores and/or canaliculi, for example, is that of allowing (by capillarity) the absorption and/or elution of the pharmaceutical or medical substances present or which can be added in the acetabular spacer device 1.

With regard to the latter aspect, in fact, it is known that a spacer, in order to eradicate the infection, has to release the pharmaceutical or medical substance adapted to the purpose in contact with the whole area of bone tissue to be treated, continuously for a certain period. Such (even small) amounts of substance, homogeneously released on the whole infected surface, act more efficiently, also with respect to larger amounts of antibiotic, whether distributed as lavage (and therefore having a short duration) and in a non-homogeneous way (and therefore not by placing an antibiotic device in contact with the whole infected zone).

The acetabular spacer device 1, as seen, being shaped similarly to the bone cavity in which it is to be implanted, and releasing the pharmaceutical or medical substance in a homogeneous continuous manner and of adequate extension, is suitable for performing this function effectively.

The acetabular spacer device 1 according to the invention is fixed to the bone tissue of the cavity in which it is to be inserted by bone cement, for example a bone cement comprising polymethyl methacrylate (PMMA) and/or similar polymers.

The projections or recesses 4 present on the first surface 2 aid the connection with the bone tissue as they determine the presence of spaces or areas in which the bone cement is somehow forced to remain, thus implementing the fixation of the device itself.

In fact, the pressure exerted by the surgeon during the operation to fix and position the acetabular spacer device 1 in its special seat can cause the movement of the bone cement placed therein. This cement, in fact, can be squashed by the spacer device and move along its peripheral portions, leaving the apical area covered and/or in contact only with a light layer of bone cement.

Thanks to the projections or recesses 4, instead, large areas of the surface 2 of the spacer device remain in contact with a suitable layer of bone cement, which remains almost trapped between one projection 4', 4" and the other or inside of the recesses 4', 4iv, thus facilitating the gluing or fixing of the device in the implantation site.

Furthermore, the projections or recesses 4 are positioned in or delimit some areas in which a greater resistance of the acetabular spacer device 1 is necessary, thus ensuring greater strength to the implantation area and avoiding the risk of the femoral or humeral head or the corresponding prosthetic or spacer components implanted at the respective cavities or joints can break through the (often thin) bone tissue found in those areas.

The acetabular spacer device 1 according to the present invention is made of biologically compatible material, such as ceramic or plastic.

With regard to plastics, it may comprise at least one thermoplastic polymer, an acrylic resin, an acrylic polymer and/or copolymer, polymethyl methacrylate, a bone cement comprising polymethyl methacrylate and/or a similar polymer.

With regard to ceramics, the material may comprise a ceramic bone cement, optionally comprising calcium sulphate ($CaSO_4$), or other components containing calcium.

In an alternative embodiment of the invention, the acetabular spacer device 1 can be made of a biologically compatible plastic and/or polymeric material such as for example polyethylene or high density polyethylene or ultra high molecular weight polyethylene (UHMWPE). In this case, the acetabular spacer device 1 can be made of such material or comprise an insert made of such material, for example placed at the second surface 3 thereof.

In fact polyethylene, and in particular UHMWPE, has self-lubricating properties and therefore increases the smoothness and/or implements the articulation with the complementary component mentioned above.

In particular, in fact, the cavity 7 is suitable for housing the head of the femur or the humerus or the head (substantially hemispherical or spherical) of the stem component (complementary to the acetabular spacer device 1) of a prosthesis or an implantable spacer device at the other end of the joint for the human body in question.

In a still alternative embodiment of the invention, the acetabular spacer device 1 is made of a composite material, that is to say, it can be made of one or more of the biologically compatible materials indicated above and comprises, inside it, a reinforcement or core (not illustrated) having a shape substantially corresponding to that of the acetabular spacer device 1, i.e. for example a cup shape.

Such internal reinforcement or core is made of a material which is structurally and/or mechanically more resistant than those constituting the outer portions of the acetabular spacer device 1, i.e. a different polymeric material or a metallic material.

In this version, the plurality of elongated projections 4 can be made in one piece with said biologically compatible material placed externally with respect to the reinforcement or core.

In a non-limiting version of the invention, the acetabular spacer device 1 can be entirely made of a plastic material or bone cement or polymethyl methacrylate.

Moreover, the biologically compatible material, as mentioned, is suitable to be additived and/or can be additived with one or more pharmaceutical or medical products, such as for example one or more antibiotics, for the reasons indicated above, for example gentamicin, vancomycin, etc. or other active ingredients. In fact, the acetabular spacer device 1, whatever the material with which it is made, comprises (and is able to elute in use, once implanted in the bone cavity in question) at least one pharmaceutical or medical substance, such as for example an antibiotic.

Such at least one pharmaceutical or medical substance may be present inside the acetabular spacer device 1 and/or be admixed thereto just before the implantation, depending on the patient's needs.

In fact, the porosity of the material allows it to be impregnated, for example by capillarity, and the subsequent release of these substances (for example prepared in the form of an aqueous solution).

One of the advantages of at least one version of the present invention is that the acetabular spacer device 1 is made of the same material as the bone cement used for fixing it to the bone tissue.

For example, if the bone cement comprises PMMA, also the biologically compatible material with which the spacer device is made comprises PMMA.

In this way, in addition to the advantages indicated above, the material constituting the acetabular spacer device 1 partially melts in contact with the bone tissue and in this way a very stable fixing between it and the bone tissue is determined, precisely by means of the cement bone that remains "trapped" in contact with its first surface 2.

It is therefore clear that the present invention guarantees an excellent and stable fixation with the bone tissue.

Furthermore, the spacer device 1 is made in one piece and therefore also the projections or recesses 4 are made in one piece with the device itself.

This also implements the stability of connection with the surrounding bone tissue.

From the foregoing description it is thus clear that the acetabular spacer device according to the present invention is able to replace any possible acetabulum of infected prostheses, preserving the articular space, an articulation surface having sufficient resistance to avoid break-through by (for example) the femoral head or corresponding components or bones in other joints of the human body and, being antibiotic-loaded and/or comprising pharmaceutical or medical substances, to treat the current infection.

Furthermore, the acetabular spacer device, being fixed to the bone tissue with a bone cement that is in turn antibiotic-loaded, acts as a local release device of at least one pharmaceutical or medical substance and/or of an antibiotic (for example Gentamicin and/or Vancomycin, etc.), promoting effective therapy to eradicate the bone infection. In this way, it is also possible to strengthen the antibiotic action of the bone cement by delivering a larger amount with the acetabular spacer device or by delivering on site a substance different from that contained in the bone tissue, expanding the coverage and/or the action spectrum against any bacteria present at the site of infection, causing the various substances to act in a synergistic way.

The device, moreover, due to its hollow hemisphere geometry, allows the articulation with the spherical head of the complementary component of the bone tissue or of the prosthesis or of the stem component of a spacer, for example of the hip, possibly of a modular type.

Therefore, the perfect geometry allows a very stable articulation with the aforementioned components, such as with the head of a hip spacer, eliminating the risks of dislocation, this risk being frequent using only the stem component of a hip spacer.

Furthermore, in this case, since the spherical head of the bone or prosthesis or of the spacer device, such as the stem component of the hip spacer, does not articulate directly on the bone of the articular cavity but on the second surface of the acetabular spacer device according to the present invention, the pain felt by the patient during the articulation is reduced and, as previously mentioned, the risk of breaking the acetabular roof—which is present in the absence of the acetabular spacer device itself—is eliminated.

Finally, the acetabular spacer device 1 according to the invention is preformed, i.e. it has a certain shape and conformation and is ready for use, without the need for the surgeon to resize, smooth or otherwise adapt it to anatomical dimensions or patient needs.

Finally, for this purpose, the acetabular spacer device 1 can be provided in several sizes, having different diameters or sections, as well as apical dimensions of a given height, so as to better adapt to the various anatomical shapes and sizes of the patient.

In particular, the acetabular spacer device 1 can be provided in 3-4 sizes. This is because it can mate with a prosthetic or spacer head (or their stem components) in an approximate way, at least in some variants thereof.

Again, at least in a version of the invention, the projections or recesses 4 are placed symmetrically with respect to a plane passing through the central symmetry axis X of the acetabular spacer device 1.

In a version of the invention, the projections or recesses 4 are positioned substantially radially with respect to the apex 6 of the acetabular spacer device 1.

In this case, the elongated projections or recesses 4 determine and/or delimit some channels, also arranged radially with respect to the apex 6 of the acetabular spacer device 1, which uniformly guide the distribution of the bone cement along the first surface 2, thereby implementing fixation thereof to the acetabular spacer device 1 and to the patient's bone.

The invention thus conceived is susceptible to numerous modifications and variations, all of which are within the scope of the inventive concept.

The features presented for a version or embodiment may be combined with the features of another version or embodiment, without departing from the scope of protection of the present invention.

Moreover, all of the details may be replaced by other technically equivalent elements. In practice, the materials used as well as the contingent size and shapes may be any according to the requirements, without departing from the scope of protection of the following claims.

The invention claimed is:

1. An acetabular spacer device adapted to be implanted during use in a bone cavity placed at a joint of a human body, said acetabular spacer device (1) comprising:
   a body made from polymethylmethacrylate and having,
      a cup shape, substantially hemispherical,
      an outer first surface (2), convex, and adapted during use to be positioned at said bone cavity, and
      an inner second surface (3), concave, which defines a cavity (7); and
   at least one pharmaceutical or medical substance, adapted to treat an ongoing infection in said bone cavity, provided within the body,
   wherein said second surface (3) is adapted to be articulated with a further stem component present at said joint of the human body, or with a head of a stem component of a corresponding permanent prosthesis or spacer device of said joint of the human body,
   wherein said outer first surface (2) comprises a plurality of elongated recesses or projections (4), that extend outward or inward with respect to said first surface (2), and that have a length (LU, LUa), a width (LA, LAa), and a height or depth (H, HA), and
   wherein at least some of said elongated recesses or projections (4) have perimeters defining a linear segment or a trapezoidal shape and extend along said outer first surface beginning from a distance larger than zero, along a solid portion of said first surface (2), from an apex (6) of said first surface (2) and define first portions and second portions of said outer first surface, said second portions being recessed in relation to said first portions and to said apex.

2. The acetabular spacer device (1) according to claim 1, wherein one or more of said elongated recesses or projections (4) depart from said apex (6) of said first surface, and extend toward or to a circular terminal perimeter of said first surface (2), or have a radial arrangement with respect to said apex (6).

3. The acetabular spacer device (1) according to claim 2, wherein said plurality of elongated recesses or projections (4) comprises a first elongated projection (4') and second elongated projections (4″), which are extended towards an exterior of said first surface (2), wherein said first elongated projection (4′) is extended along a portion of an outer circumference of said first surface (2) crossing said apex (6), wherein said second elongated projections (4″) are radially placed with respect to said apex (6) and/or are spaced from said apex (6) by a distance (Y), and wherein said first and second elongated projections (4′, 4″) have said length (LU) greater than said width (LA).

4. The acetabular spacer device (1) according to claim 2, wherein said first and second surfaces (2, 3) are substantially coaxial and have a central symmetry axis (X) which coincides with a central symmetry axis of said acetabular spacer device (1).

5. The acetabular spacer device (1) according to claim 4, further comprising a base (5), perpendicular to said central symmetry axis (X), and wherein said apex (6) of said first surface is opposite to said base (5) and is positioned at a top point of said first surface (2).

6. The acetabular spacer device (1) according to claim 5, wherein said base (5) comprises a base ring (5a), which connects said first surface (2) and said second surface (3), or which connects said circular terminal perimeter of said first surface (2) and a terminal circular perimeter of said second surface (3), and delimits an inlet opening (5b) towards said second surface (3) and of said cavity (7).

7. The acetabular spacer device (1) according to claim 6, further comprising, at said base (5) and/or at said terminal circular perimeter of said first surface (2), an annular tab (8) which extends outwardly for a distance (Z) with respect to said acetabular spacer device (1) and/or with respect to said first surface (2).

8. The acetabular spacer device (1) according to claim 1, wherein said outer first surface (2) comprises said plurality of elongated recesses, and wherein said elongated recesses (4, 4‴) recess towards an interior of said body and have, at least in a middle portion between the apex and an outer edge of the acetabular spacer device, a constant cross-section, said elongated recesses being radially placed with respect to said apex (6) and/or spaced from an apex (6) of said first surface by a said distance (Y) greater than zero, and wherein said elongated recess extend toward said outer edge starting from a recessing groove (4c), placed around said apex (6) and having an annular circular shape.

9. The acetabular spacer device (1) according to claim 8, wherein said recessing groove (4c) delimits, at said apex (6), a zone (4d) of said first surface (2) having a circular shape, and/or wherein said elongated recesses (4, 4″) delimit angular sectors (2d), of said first surface (2), having a triangular shape, with a vertex at said recessing groove (4c) and base at a portion of a circular terminal perimeter of said first surface (2).

10. The acetabular spacer device (1) according to claim 1, wherein said plurality of elongated recesses or projections (4) comprises elongated recesses (4, 4iv), recessing towards an interior of said first surface (2) and having a polygonal or ovoidal shape, with a width (LAa) that increases moving away from said apex (6) towards a circular terminal perimeter of said first surface (2) and/or a length (LUa) equal to substantially 1-2 times a maximum width (LAa) of said elongated recesses.

11. The acetabular spacer device (1) according to claim 10, wherein said elongated recesses (4, 4iv) delimit, at said apex (6), a zone (4d) of said first surface (2) having a circular or polygonal shape, or wherein said elongated recesses (4, 4iv) delimit angular sectors (2d), of said first surface (2), having a triangular or trapezoidal shape, with a vertex or smaller base at said zone (4d) and a greater base at a portion of said circular terminal perimeter of said first surface (2).

12. The acetabular spacer device (1) according to claim 1, wherein said first surface (2) has a shape substantially complementary to a shape of said bone cavity, or wherein said second surface (3) is smooth, in order to facilitate articulation during use, or wherein said first and second surfaces (2, 3) are substantially hemispherical.

13. The acetabular spacer device (1) according to claim 1, wherein said acetabular spacer device (1) is integrally made with said elongated recesses or projections (4), is preformed, and said polymethylmethacrylate comprises pores and/or canaliculi with dimensions smaller than 100 micrometers.

14. The acetabular spacer device (1) according to claim 1, wherein said acetabular spacer device (1) comprises an insert made of a plastic or polymeric biologically compatible material placed at said second surface (3).

* * * * *